US00PP32653P2

(12) United States Plant Patent
Hansen

(10) Patent No.: US PP32,653 P2
(45) Date of Patent: Dec. 15, 2020

(54) ***ECHINACEA* PLANT NAMED 'CANARY FEATHERS'**

(50) Latin Name: ***Echinacea* hybrid**
Varietal Denomination: Canary Feathers

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/873,019

(22) Filed: Jan. 15, 2020

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson

(57) ABSTRACT

The new and distinct cultivar of *Echinacea* plant named 'Canary Feathers', with fragrant inflorescences on strong well-branched stems producing single whorls of broadly-overlapping, bright yellow ray florets that maintain their coloration with little change through maturity. The large inflorescence cones have pronounced dark cones with effective colors ranging from yellowish-green to orangish-yellow. The new plant flowers from mid-summer to late summer, and is suitable as a potted plant, for the landscape, and for cut flower arrangements.

1 Drawing Sheet

Botanical denomination: *Echinacea* hybrid.
Cultivar designation: 'Canary Feathers'.

STATEMENT REGARDING PRIOR DISCLOSURES UNDER 37 CFR 1.77(B)(6)

The first non-enabling disclosure of the claimed plant, in the form of a photograph and brief description was on a website operated by Walters Gardens, Inc. on Feb. 1, 2019. *Echinacea* 'Canary Feathers' was listed with a photograph and brief description in the "Walters Gardens 19-20 Catalog" distributed first on May 29, 2019. The claimed plant was first sold on Jul. 8, 2019 by Walters Gardens, Inc., who obtained the plant and all information relating thereto, from the inventor. No plants of *Echinacea* 'Canary Feathers' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'Canary Feathers'. The new plant was the result of a self-pollination by the inventor of the proprietary hybrid known only by the breeder code as 14-3-11 (not patented) on Jul. 15, 2015 at a wholesale perennial nursery in Zeeland, Mich. This seedling was evaluated first in trials in the summer of 2016 at the same nursery and assigned the breeder code of 15-3-7. *Echinacea* 'Canary Feathers' has been asexually propagated at the same nursery by crown division since 2017 and also using careful shoot tip tissue culture procedures and found to reproduce plants that exhibit all the characteristics identical to the original plant.

*Echinacea* 'Canary Feathers' is distinct from all other Coneflowers known to the inventor. The nearest comparison cultivars are 'Matthew Saul' U.S. Pat. No. 17,652, 'Leilani' U.S. Plant Pat. No. 23,526, 'Maui Sunshine' U.S. Plant Pat. No. 22,808, 'Balsomemy' U.S. Plant Pat. No. 24,768, 'Balsomemyim' U.S. Plant Pat. No. 30,116, 'Julia' U.S. Plant Pat. No. 24,629, 'Cleopatra' U.S. Plant Pat. No. 24,631, 'TNECHKY' U.S. Plant Pat. No. 29,922 and its sister sibling to the new plant 'Yellow My Darling' U.S. Plant patent application Ser. No. 16/602,732.

The parent plant, 14-3-11, was not maintained as either plants or in photography, so no comparison is possible. 'Matthew Saul' has ray florets that are more orangish-yellow and produces much smaller inflorescences. 'Leilani' is slightly taller in habit and ray florets have a more gold to orangish-yellow color. 'Maui Sunshine' is much taller in habit and has narrower ray florets that are less overlapping and the receptacle spines are more orange in color. 'Balsomemy' has ray florets that are strong orange in color and tend to droop more as they mature. 'Balsomemyim' produces plants with a shorter habit, the stems produce no branching with ray florets that are more yellowish-green. 'Julia' has ray florets and receptacle spines that are more tangerine orange on shorter stems. 'Cleopatra' has a shorter habit with ray florets that lighten more with age to a creamy-yellow. 'TNECHKY' has a slightly taller habit, smaller inflorescences, the ray petals are orangish-yellow and droop more with maturity. 'Yellow My Darling' is slightly taller in habit, the ray florets lighten to a creamy yellow.

SUMMARY OF THE INVENTION

*Echinacea* 'Canary Feathers' has not been evaluated under all possible environmental conditions. The phenotype may vary with variations in environment including: growing temperature, available sunlight, nutrients, water, etc. without a change in the genotype of the plant. The new plant is distinct from its parents and all other *Echinacea* known to the applicant in the following combined traits:

1. Fragrant inflorescences on strong well-branched stems;
2. Large, broad inflorescences with single whorl of ray florets that tend to stay horizontal once open;
3. Ray petals are wide and broadly-overlapping;
4. Ray petals of bright yellow with dark cones;
5. Vigorous growth and excellent habit;
6. Olive-green lanceolate foliage.

BRIEF DESCRIPTION OF THE DRAWINGS

The photographs of the new invention demonstrate the overall appearance of the plant including the unique traits. The drawings of the new plant are of a two-year-old plant grown in full-sun trial garden in Zeeland, Mich. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
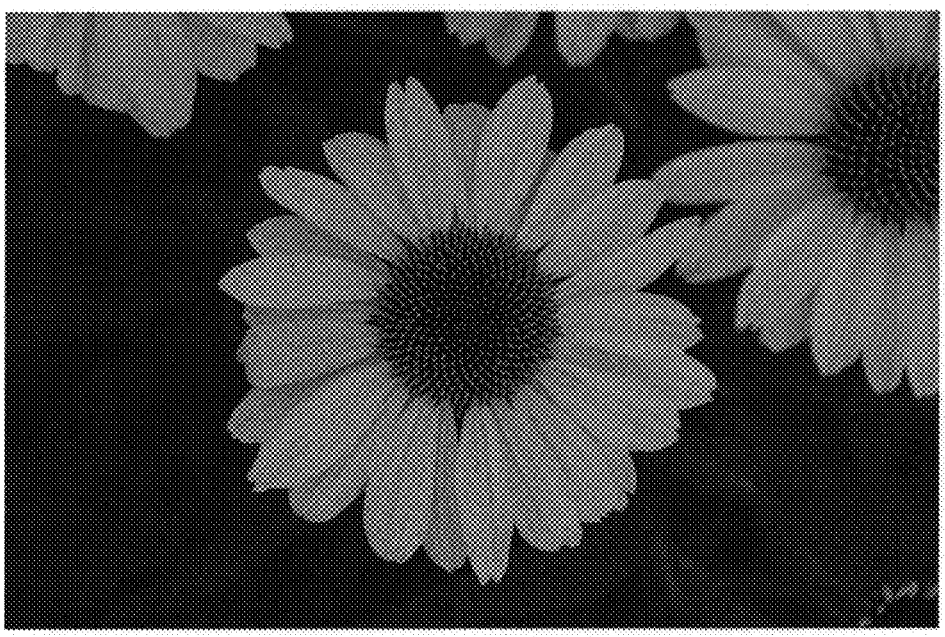
FIG. 1 shows a close up of some inflorescences of the new plant.
Figure 2:
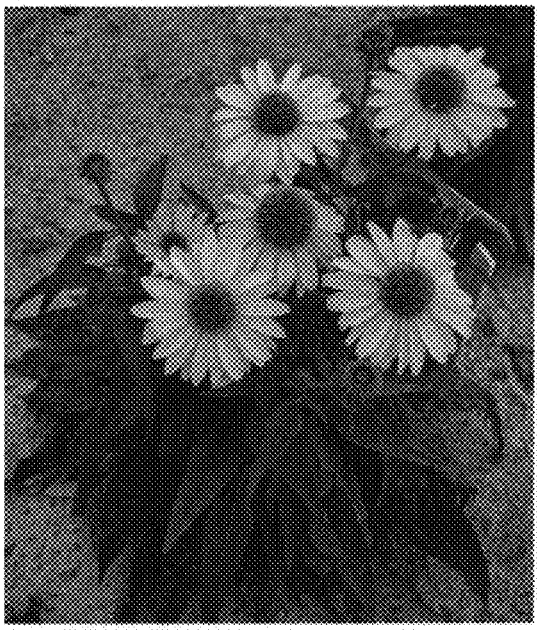
FIG. 2 shows the habit of the new plant in flower.

The following description of *Echinacea* 'Canary Feathers' is based on observations of two-year-old specimens grown in a full-sun trial garden with supplemental water and fertilizer in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female and male parent is the proprietary unreleased hybrid 14-3-11;

Plant habit: Multi-stemmed, freely-branched, hardy herbaceous perennial, flowering to about 54.0 cm tall and foliage to 34 cm tall and 56 cm wide;

Growth rate: Vigorous, finishing in 4 liter containers in about 2 months during the summer;

Roots: Cream-colored, finely branched; color nearest RHS NN155B depending on soil;

Foliage: Alternate; lanceolate; acute apex; attenuate base; margin serrate, micro-ciliolate; micro-puberulent abaxial and adaxial; to about 12.0 cm long and 4.5 cm wide decreasing distally, average about 11.0 cm long and 3.8 cm wide; variegation absent;

Leaf color: Young leaves adaxial between RHS 144A and RHS 146C, abaxial between RHS 144B and RHS 146C; mature leaves adaxial nearest NN137A, abaxial between RHS 146A and RHS 147B;

Foliage fragrance: Lightly herbal;

Venation: Pinnate; with two major arcuate veins on both sides of the midrib; abaxial midrib and veins costate; glabrous adaxial, sparsely hirsutulous abaxial;

Vein color: Adaxial primary veins between RHS 138B and RHS 138C, secondary veins nearest RHS NN137A; abaxial primary veins between RHS 146D and RHS 145A, secondary veins nearest RHS 137A;

Petiole: Concavo-convex, strigillose adaxial and sparsely puberulent to strigillose abaxial; about 12.0 cm long and 3.0 mm wide on lowest leaves and decreasing to sessile distally; color nearest RHS 145A adaxial and abaxial nearest RHS 146D;

Peduncle: Densely puberulent; cylindrical; strong stiff; average 25.0 cm long and 8.0 mm diameter; quantity per plant about nine; flowering in upper 30 cm;

Peduncle color: Nearest RHS 146D;

Branches: Cylindrical, strigillose; tightly angled to main stem to about 60° above horizontal: to about 22 cm long and 4.5 mm diameter; color nearest RHS 146D;

Inflorescence: Bracteate head, aggregate of achene; with single whorl of distinct ligulate ray florets and central disk florets in a pappus; flowering mid-summer to late summer; initial flowers largest, to about 9.5 cm wide, average about 8.0 cm diameter with cones 2.7 cm across and 3.7 cm tall; approximately 5 inflorescences per peduncle;

Inflorescence fragrance: Lightly sweet;

Flower persistence: Remaining affective in color for 10 to 14 days depending on temperatures, cone drying on plant and effective into winter;

Involucre: With numerous bracts; about 50 per inflorescence in 3 whorls; arcuate downward toward peduncle;

Involucre bracts: Lanceolate to linear; narrowly acute apex; truncate base; micro-ciliolate margin; adaxial glabrous and lustrous; abaxial micro-puberulent; average about 12.0 mm long and 3.0 mm across; color nearest RHS 148D adaxial center, basal margin nearest RHS 155A, distally between RHS NN137A and RHS 139A; abaxial center nearest RHS NN137A, abaxial margins nearest RHS 146D;

Inflorescence buds with ray florets vertical and still enrolled: About 33.0 mm across and 23.0 mm tall; ray floret color nearest RHS 145A adaxial with spines nearest RHS 136B and nearest a blend of RHS 136A and RHS 200A proximally;

Ray florets: Zygomorphic; arrangement in single whorl, broadly-overlapping, typically imbricate; lanceolate, apex emarginated with two or more notches to 1.0 mm deep; base cuneate; margin entire; adaxial lustrous and glabrous; abaxial matte and glabrous; 19 to 27 per inflorescence; opening to horizontal, drooping up to only 10 degrees below horizontal with maturity; pistillate; astemonous; ligule to 40.0 mm long and 13.0 mm wide, average size 37.0 mm long, 12.5 mm wide near center tapering to 2 mm wide in basal 3 mm; thickened veins raised; twisting absent;

Ray ligule color: When first horizontal—adaxial nearest RHS 13A, base nearest RHS 145D; abaxial nearest RHS 8C with base nearest RHS 145D; before dehiscence—adaxial nearest 8A and abaxial nearest 8C with adaxial and abaxial base nearest RHS 4D;

Disc florets: About 200 to 350 per head; actinomorphic; perfect; synandrous; produced in raised dome, about 4.0 cm across and 3.5 cm tall; individually to about 11.0 mm long to exserted style and 2.0 mm diameter;

Corolla: Fused forming tube; outer florets about 7.0 mm long and 1.5 mm wide, central florets about 6.0 mm long and 1.5 mm wide; fused in basal 5.0 to 6.0 mm, free in distal 1.0 mm; individual tepals about 0.5 mm wide at fusion; acute apex; entire margin; surfaces slightly lustrous;

Corolla tube color: Adaxial nearest RHS N144D and abaxial nearest RHS 144D;

Disk floret androecium: Five; synandrous;

Staminal column: About 1.0 mm wide and protrudes from corolla tube about 2.0 mm; five connate stamens;

Anthers: Fused, about 3.5 mm long and 0.7 mm diameter; color alternating stripes of nearest RHS 162C and RHS 202A;

Filaments: Five; attached to column; thin, less than 0.2 mm diameter and 0.5 mm long; color nearest RHS NN155C;

Pollen: Globose, abundant, less 0.1 mm in diameter, RHS 17B;

Gynoecium: Single; to 7.0 mm long;

Style: About 4.0 mm long and 0.2 mm diameter; color between RHS 145B and RHS 150D proximally;

Stigma: Not split; reflexed about 180°; about 2.0 mm long and 0.2 mm diameter; color nearest RHS 145D;

Fruit: Not observed;

Receptacle pines: With disk florets; acicular; to 12 mm long and 2.0 mm diameter;

Spine color: Adaxial and abaxial nearest RHS 17B distally and between RHS 145C and RHS 145D proximally; after ray ligules fall between RHS 163B and RHS 163C;

Disease resistance: Resistance beyond that of other hardy Coneflower cultivars has not been observed. The plant grows best with plenty of moisture and adequate drainage, but is able to tolerate some drought when mature. Hardiness at least from USDA zone 4 through 8.

I claim:

1. A new and distinct ornamental cultivar of *Echinacea* plant named 'Canary Feathers' as herein described and illustrated.

* * * * *